United States Patent [19]
Roberts

[11] Patent Number: 6,110,726
[45] Date of Patent: Aug. 29, 2000

[54] ACTINOMYCETE STRAINS OF ATCC 55984 AND USES THEREOF FOR GROWTH ENHANCEMENT AND CONTROL OF PATHOGEN INFECTION IN PLANTS

[76] Inventor: Mark A. Roberts, 310 Spotswood, Moscow, Id. 83843

[21] Appl. No.: 09/113,424

[22] Filed: Jul. 10, 1998

Related U.S. Application Data

[60] Provisional application No. 60/052,129, Jul. 10, 1997.

[51] Int. Cl.$^7$ ............... C12N 1/20; C12N 1/00; A01N 63/00
[52] U.S. Cl. ............... 435/252.4; 435/253.5; 435/886; 424/93.43
[58] Field of Search ............... 424/93.43; 435/252.4, 435/253.5

[56] References Cited

U.S. PATENT DOCUMENTS

| | | | |
|---|---|---|---|
| 4,534,965 | 8/1985 | Brown et al. | 424/93 |
| 5,527,526 | 6/1996 | Crawford | 424/93.43 |

OTHER PUBLICATIONS

El–Shanshoury et al., "Effects of *Streptomyces corchorusii, Streptomyces mutabilis*, pendimethalin, and metribuzin on the control of bacterial and Fusarium wilt of tomato", Can. J. Bot., 1996, 74, pp. 1016–1022.

Aldrich, J., and Baker, R. 1970. Biological control of *Fusarium roseum* f. sp. *dianthi* by *Bacillus subtilis*. Plant Disease Reporter. 54:446–448.

Bibb, M.J., Ward, J.M., and Cohen, S.N. 1985. Nucleotide sequences encoding and promoting expression of three antibiotic resistance genes indigenous to *Streptomyces*. Mol. Gen. Genet. 199:26–36.

Broadbent, P., Baker, K.F., and Waterworth, Y. 1971. Bacteria and antinomycetes antagonistic to fungal root pathogens in Australian soils. Aust. J. Biol. Sci. 24:925–944.

Caballero, J.L., Malpartida, F., and Hopwood, D.A. 1991. Organisation and functions of the actVA region of the actinorhodin biosynthetic gene cluster of *Streptomyces coelicolor*. Mol. Gen. Genet. 228:372–380.

Chater, K.F. 1992. Genetic regulation of secondary metabolic pathways in Streptomyces. CIBA Found. Symp.. 171:144–162.

Chater, K.F., and Hopwood, D.A. 1989. Antibiotic biosynthesis in Streptomyces. In: Genetics of Bacterial Diversity. D.A. Hopwood and K.F. Chater (eds.) Genetics of Bacterial Diversity. pp. 129–150. Academic Press, London.

Dazzo, F.B. 1980. Microbial adhesion to plant surfaces. In: Microbial Adhesion of Surfaces. J.M. Lynch, J. Melling, P.R. Rutter, and B. Vincent (eds). pp. 311–328. Ellis Horwood, Chichester.

Distler, J., Brown, C., Ebert, A., and Piepersberg, W. 1987. Gene cluster for streptomycin biosysthesis in *Streptomyces griseus*: analysis of a central region including the major resistance gene. Mol. Gen. Genet. 208:204–210.

Gil, H.A., Kieser, H.M., and Hopwood, D.A. 1985. Cloning of a chloramphenicol acetyltransferase gene of *Streptomyces acrimycini* and its expression in Streptomyces and *Escherichia coli*. Gene. 38:1–8.

Hale, M.G. and Moore, L.D. 1979. Factors affecting root exudation II: 1970–1978. Adv. Agron. 31:93–124.

Hale, M.G., Moore, L.D., and Griffin, G.J. 1978. Root exudates and exudation. In: Interactions between non–pathogenic soil microorganisms and plants. Y.R. Dommergues and S.V. Krupa (eds.). pp. 163–204. Elsevier, Amsterdam.

Howell, C.R., and Stipanovic, R.D. 1980. Suppression of *Pythium ultimum*–induced damping–off of cotton seedlings by *Pseudomonas fluorescens* and its antibiotic, pyroluteorin. Phytopath. 70:712–715.

Lawley, R.A., Campbell, R., and Newman, E.I. 1983. Composition of the bacterial flora of the rhizosphere of three grassland plants grown separately and in mixtures. Soil Biol. Biochem. 15:605–607.

Lawley, R.A., Newman, E.I., and Campbell, R. 1982. Abundance of endomycorrhizas and root–surface microorganisms on three grasses grown separately and in mixtures. Soil Biol. Biochem. 14:237–240.

Lockwood, J.L. 1973. Fungistasis in soils. Biol. Rev. 52:1–43.

Neal, R.J. and Chater, K.F. 1991. Bidirectional promoter and terminator regions bracket mmr, a resistance gene embedded in the *Streptomyces coelicolor* A3(2) gene cluster encoding methylenomycin production. Gene 100:75–83.

Rovira, A.D. 1979. Biology of the soil–root interface. In: The Soil–Root Interface. J.L. Harley and R.S. Russell (eds). pp. 146–160. Academic Press, London.

Rovira, A.D. 1965. Plant root excretions in relationship to the rhizosphere effect. In: Ecology of Soil–borne Plant Pathogens. K.F. Baker and W.C. Snyder (eds.). pp. 170–184. Univ. of Calif. Press, Berkeley, CA.

Rovira, A.D. 1956. Plant root excretions in relationship to the rhizosphere effect. I. The nature of root exudates from oats and peas. Plant Soil. 7:178–194.

Smibert, R.M. and Krieg, N.R. 1994. Phenotype characterization. In: methods for General and Molecular Biology. P. Gehardt, R.G.E. Murray, W.A. Wood, N.R. Krieg (eds.). p. 623. American Society of Microbiology Washington, D.C.

(List continued on next page.)

*Primary Examiner*—Irene Marx
*Assistant Examiner*—Vera Afremova

[57] ABSTRACT

One or more identified biologically pure strains of Actinomycete isolated from ATCC 55984 and methods of using the strains. The strains are used to confer protection against plant pathogen infection in a susceptible plant and are also used to enhance growth in a responsive plant. The methods of use include contacting at least a plant part, soil or soil-less potting mixture with a composition that includes at least one of the identified strains of Actinomycetes.

19 Claims, 2 Drawing Sheets

OTHER PUBLICATIONS

Thomashaw, L.S., and Weller, D.M. 1996. Current concepts in the use of introduced bacteria for biological disease control and mechanisms and antifungal metabolites. In: Plant–Microbe Interactions. G. Stacey and N.T. Keen (eds.). v. 1. Chapman and Hall, New York, NY.

Utkhede, R.S., and Rahe, J.E. 1983. Interactions of antagonist and pathogen in biological control of onion white rot. Phytopath. 73:890–893.

Vancura, V. and Hovadik, A. 1965. Plant Microbes Relationships. J. Macura and V. Vancura (eds.). p. 21. Czech. Acad. Sci., Prague.

Williams, S.T., Goodfellow, M., Alderson, G., Willington, E.M.H., Sneath, P.H.A. and Sackin, M. (1983a). Numerical classification of *Streptomyces* and related genera. J. Gen. Microbiol. 129:1743–1813.

Williams, S.T., Goodfellow, M., Wellington, E.M.H., Vickers, J.C., Alderson, G., Sneath, P.H.A., Sackin, M. and Mortimer, A.M. (1983b). A probability matrix for the identification of some streptomycetes. J. Gen. Microbiol. 129:1815–1830.

ACTINOMYCETE STRAINS OF ATCC 55984 AND USES THEREOF FOR GROWTH ENHANCEMENT AND CONTROL OF PATHOGEN INFECTION IN PLANTS

RELATED APPLICATIONS

This application claims the priority of Provisional Application Ser. No. 60/052,129, entitled Biological Control Of Fungal Diseases And Other Pests As Well As Crop Improvements By Individual Or Mixed Cultures Of Streptomyces Sp., Or Other Similar Actinomycetes Or Their Genes, filed Jul. 10, 1997.

FIELD OF THE INVENTION

The present invention relates to new strains of actinomycetes including Streptomyces bacteria that are capable of inhibiting the growth of soil borne plant pathogens and thereby enhancing plant growth.

BACKGROUND OF THE INVENTION

The present invention relates to the control of fungal and/or bacterial infections of plants by actinomycetes that are antagonistic to, or produce materials antagonistic to undesired fungi or bacteria.

Fungal or bacterial phytopathogens are a cause of substantial economic losses in the agriculture, forestry, and horticulture industries. It is estimated that approximately four billion dollars are lost annually to disease. Many types of plant pathogens have been described including those that cause disease symptoms called damping-off, root-rot, wilt, blights, or stem and leaf rots. Such diseases can kill emerging seedlings, reduce plant robustness, and adversely affect crop yields.

Traditionally, breeding for resistant plants, sterilizing the soil either physically (e.g. steam) or chemically (e.g. methyl bromide fumigation) or chemical fungicide application has been attempted for control of phytopathogens. However, each of these methods has serious drawbacks. Completely resistant cultivars have not been developed. Soil sterilization is expensive and removes beneficial microorganisms that naturally compete against phytopathogens. Methyl bromide fumigation is being regulated out of existence. The use of chemical fungicides or bacteriostats to control phytopathogens has come under closer scrutiny due to their expense, lack of efficacy, limited effective duration, emergence of resistant pathogens, and regulation. Additionally, the use of chemicals for pathogen eradication is not desirable due to their toxicity to humans and the environment.

Biological control of plant pathogens is defined as the use of one or more biological processes to lower inoculum density of the pathogen or reduce its disease producing activities. The mechanisms underlying these processes include competitive exclusion of the pathogens(s), antibiosis, mycoparasitism, or induced resistance of the plant.

Microbial control as a means for protecting plants from pathogens provides an advantage over traditional control measures in that the biocontrol microorganisms grow and proliferate under conditions favorable for plant growth. Thus the effective concentration of the control agent can increase during the growing season, rather than decrease, as occurs with chemical control measures. The environment is not unduly degraded, and may in fact be upgraded, in that these microorganisms are a natural constituent of the environment and supply essential nutrient cycling functions. Due to the multiple mechanistic nature of biological control, the possibility of pathogens acquiring resistance to these controls are either eliminated (competitive exclusion, mycoparasitism) or drastically reduced (antibiosis). Furthermore, it is an established fact that plants may acquire microbial-mediated resistance factors towards the pathogen (induced resistance), thus providing a secondary defense mechanism.

Members of the Actinomycetales family are especially useful as biological agents for reducing phytopathogen infection in that they produce over 60% of the approximately 5,000 known antibiotics, some strains synthesizing 30 or more including many with fungicidal activity. They produce an enormous diversity of hydrolytic enzymes including enzymes that degrade fungal cell wall components, such as chitinases, cellulases, and glucanases. They are heterotrophically diverse, as they are evolutionarily adapted for growth in the soil or in close proximity to plant roots utilizing a wide range of carbon sources. They produce spores under environmental deleterious conditions. They grow vegetatively as mycelia, thus allowing root colonization and translocation of nutrients over relatively large distances.

The object of the present invention is to provide a new biological control means of reducing fungal or bacterial pathogen infection of plants.

SUMMARY OF THE INVENTION

The invention has been achieved by the isolation of a number of actinomycete bacteria that have been screened against specific phytopathogens and are effective in inhibiting their growth. These actinomycetes hereby described and identified herein and referred to as IBS-24, are biologically pure cultures and have been deposited on Jun. 19, 1997 as a single effective mixture at American Type Culture Collection, 10801 University Boulevard, Manassas, Va., 20110-2209, and identified as ATCC 55984.

The present invention also sets forth various compositions suitable for treating soil, seeds, plant roots, soil-less potting mixtures, other plant parts, or foliage of plants. Such compositions maintain the viability of the active antagonist component or substance, can be effectively applied to soil, seed, roots, or foliage, provide mineral or nutrient sources for the germination and vegetative growth of the actinomycetes, and reduce the susceptibility of plants to fungal or bacterial infections.

In an exemplary embodiment, such compositions comprise a biologically pure strain or mixture of actinomycete strains and a delivery medium. A soluble medium includes the actinomycete spores homogeneously mixed with dry powdered milk or powdered whey at a spore concentration of $1 \times 10^8$ colony forming units (CFU)/g medium. The delivery medium serves as a physical support for the bacteria and as a carbon and nitrogen source for spore germination and vegetative proliferation of the bacteria once wetted. Once solubilized, this composition may be incorporated into a drench treatment utilizing existing drench equipment, for example, on turf or plant nursery stock. The composition may also be used directly to coat seeds, roots, soil or soil-less mixture, or foliage, either in its dry or solubilized form.

In another embodiment, the compositions comprise a biologically pure strain or mixture of actinomycete strains in an insoluble delivery medium. The delivery medium may be, for example, zeolite or talc. In one embodiment, the medium comprises spores at a concentration of $1 \times 10^6$ CFU/g medium to 1×10⁸ CFU/g medium. The composition may be dusted on plant roots, amended directly into soil or soil-less potting mixtures, or applied to seeds or foliage.

In another embodiment, the compositions comprising a pure actinomycete spore culture or cultures may be combined with supplements to enhance plant growth, such as fertilizers or other forms of plant nutrients. Other supplements to further reduce pest or disease damage may also be utilized including chemical pesticides, fungicides, or other biological control agents.

DETAILED DESCRIPTION OF THE INVENTION

Figure 1:
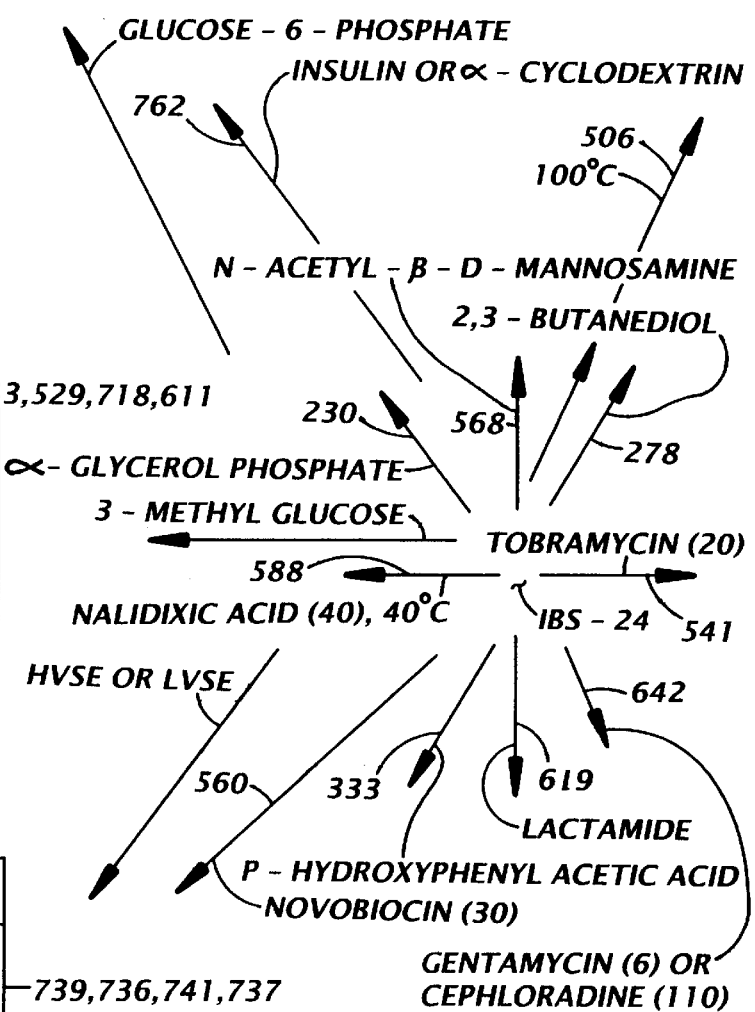
FIG. 1 is a flow chart illustrating the steps to accomplish the isolation of individual strains of Actinomycete of the present invention out of the consortiom deposit ATCC 55984.

The present invention describes the isolation of a number of actinomycete strains from soil and plant rhizosphere. Twenty four actinomycete strains are described herein and have been submitted as a consortium as ATCC 55984. The described isolated strains show a high level of antagonism towards plant pathogens, possess prolific spore generation, and have desirable physiological and morphological dissimilarities. It is believed that mutants of the described strains possess the same properties and substantially the same identifiable characteristics and would therefore represent a biologically same strain as the numbered strains described herein. It is highly unlikely that any two of these strains are clones in that over 4000 different genomes may be present in a single gram of soil. Also, these strains were isolated under differing culture conditions and from different plant roots, soils, and locations as shown in Table 1 below. Soil and rhizosphere samples were air-dried, homogenized, and serially diluted onto the specific isolation agar. Colonies exhibiting actinomycete morphology were picked from agar plates and re-streaked for isolation onto PDA to verify purity.

TABLE 1

| Isolated Strain | [1]Temp (° C.) | [2]Location | [3]Media | [4]Niche | [5]Trt |
|---|---|---|---|---|---|
| 125 | 30 | A | PDA | 1 | No |
| 226 | 30 | B | SPA | 1 | No |
| 230 | 30 | C | PDA | 1 | No |
| 278 | 30 | D | PDA | 1 | No |
| 302 | 30 | E | PDA | 1 | No |
| 333 | 30 | F | PDA | 1 | No |
| 506 | 100 | G | YCED | 1 | No |
| 529 | 40 | H | GA | 1 | No |
| 541 | 40 | H | GA | 1 | No |
| 560 | 40 | I | GA | 2 | No |
| 568 | 40 | J | H₂O | 3 | No |
| 588 | 40 | K | H₂O | 4 | No |
| 611 | 50 | L | H₂O | 5 | No |
| 619 | 25 | J | PDA | 3 | No |
| 642 | 25 | M | PDA | 6 | No |
| 643 | 25 | N | GA | 7 | No |
| 668 | 50 | O | PDA | 8 | No |
| 718 | 110 | P | SC | 9 | No |
| 736 | 25 | P | HVSE | 9 | M6 |

TABLE 1-continued

| Isolated Strain | [1]Temp (° C.) | [2]Location | [3]Media | [4]Niche | [5]Trt |
|---|---|---|---|---|---|
| 737 | 25 | P | ND | 9 | M2 |
| 738 | 25 | P | LVSE | 9 | M6 |
| 739 | 25 | P | LVSE | 9 | M6 |
| 741 | 25 | P | HVSE | 9 | M7 |
| 762 | 110 | Q | HVSE | 10 | M6 |

[1]Temperature (° C.) at which the soil samples containing presumptive actinomycetes were pre-treated prior to dilution plating and isolation.
[2]Location from which the actinomycetes were collected. A Nevada desert soil, B-F Priest River Experimental forest floor, Priest River, Idaho. Each letter indicates a different location within the forest, as denoted by a number. B location #5, C location #6, D location #21, E location #29, F location #34. G-H naturally suppressive soil, potato field, Idaho Experiment Station, Aberdeen, ID. G location #1, H location #2. I-O Vegetable trial plots, each letter indicating a different position in the field. I location #11, J location #13, K location #26, L location #32, M location #28, N location #1, O location #3. P-Q organic garden, Moscow, ID. P location #1, Q location #2.
[3]Media which the actinomycetes were initially isolated on. PDA, potato dextrose agar (Sigma). SPA, sporulation agar consisting of yeast extract (1.0 g/L), tryptose (2.0 g/L), glucose (10.0 g/L), beef extract (1.0 g/L), FeSO₄ (trace), and agar (18.0 g/L), pH adjusted to 7.0. YCED, yeast extract, casamino acids, dextrose containing yeast extract (0.3 g/L), casamino acids (0.3 g/L), D-glucose (0.3 g/L), K₂HPO₄ (2.0 g/L) and agar (18.0 g/L), pH 7.0. GA, glucose asparagine consisting of glucose (10.0 g/L), asparagine (0.5 g/L), K₂HPO₄ (0.5 g/l), agar (18.0 g/L), pH 7.0. H₂O, water agar consisting of water (1.0 L) and agar (18.0 g/L). SC, starch casein agar consisting of soluble starch (10.0 g/L), casein (1.0 g/L), K₂HOP₄ (0.5 g/L) and agar (18.0 g/L) pH 7.0. HVSE, humic acid, vitamin, soil extract agar consisting of humic acid (1.0 g/L), Na₂HPO₄ (0.5 g/l), KCl (1.7 g/L), MgSO₄7H₂O (0.05 g/L), FeSO₄7H₂O (0.01 g/L), CaCO₃ (0.02 g/L), yeast extract (0.15 g/l), and soil extract (50.0 g soil in 500 ml water, steam heated for one hour, filtrate used as the amendment), 100 ml/L. ND, not determined. LVSE, lignin, vitamin, soil extract agar consisting of all constituents of HVSE agar with lignin substituted for humic acid. These media are primarily used for actinomycete isolation from environmental samples.
[4]Environmental niche from which the actinomycetes were initially isolated. 1 bulk soil, 2 garbonzo bean rhizosphere, 3 Spanish brown lentil rhizosphere, 4 black-eye pea variety #1 rhizosphere, 5 lettuce rhizosphere, 6 black-eye pea variety #2 rhizosphere, 7 Oregon sugar pod pea rhizosphere, 8 Columbia pea rhizosphere, 9 tomato rhizosphere, 10 basil rhizosphere.
[5]Chemical or antibiotic treatment used for actinomycete isolation. Each class of treatment is semi-selective for a different group of actinomycete. M6 nystatin (50 µg/ml), cycloheximide (50 µg/ml), and nalidixic acid (20 µg/ml). M2 nystatin (50 µg/ml),cyclohexamide (50 µg/ml), norfloxacine (20 µg/ml), nalidixic acid (20 µg/ml), and polymyxin B (5 µg/ml). M7 nystatin (50 µg/ml), cycloheximide (50 µg/ml), nalidixic acid (20 µg/ml), and novobiocin (20 µg/ml). After autoclaving each of these antibiotics were added to the specified media to the final concentration indicated in parentheses.

The actinomycete strains of the present invention are potent biological control agents. These strains effectively inhibit the growth of a diversity of fungal and bacterial plant pathogens. They exhibit strong antagonism towards a wide range of pathogens causing pre- and post-emergence damping off of seedlings, root rot, blights, molds, crown rot, bacterial spot and wilt. Antagonism bioassays were employed as a screening procedure to determine growth inhibition of a large number of virulent plant pathogens, table 2.

TABLE 2

| Plant pathogen | Disease, host plant |
|---|---|
| *Fusarium oxysporum* | Fusarium crown and root rot of tomato, damping off and root rot of conifers, root rot and basal bulb rot of onion |

TABLE 2-continued

| Plant pathogen | Disease, host plant |
| --- | --- |
| Rhizoctonia solani | Damping-off, root rot, and basal stem rot of tomato, damping off of conifers |
| Whetzelinia sclerotiorum | White mold of tomato |
| Alternaria solani | Early blight, tomato |
| Phytopthora infestans | Late blight, potato |
| Gauemannomyces graminis | Take-all, wheat, turf |
| Colletotrichum spp. | Black dot, anthracnose, potato |
| Pythium ultimum | Damping-off, eggplant, conifers |
| Sclerotium cepivorum | White-rot, onion |
| Pyrenochaeta terrestris | Pink-root, onion |
| Macrophomina phaseolina | Charcoal root rot, conifer |
| Heterobasidion annosum | White rot, conifer |
| Botrytis cinerea | Gray mold, conifer; Botrytis bunch rot, grapes |
| Phytopthora pseudotsugae | Root rot, conifer |
| Phytopthora cryptogea | Root rot, conifer |
| Streptomyces scabies | Potato scabies |
| Xanthomonas campestris | Bacterial spot, tomato |
| Burkholderia solanacearum | Bacterial wilt, tomato |
| Burkholderia syringae | Bacterial wilt, tomato |
| Armillaria ostyoae | Shoestring root rot, conifer |
| Sclerotinia homoeocarpa | Dollar spot, turf |
| Rhizoctonia solani | Brown patch or Rhizoctonia blight, turf |
| Pythium aphanidermatum | Pythium blight, turf |
| Microdochium nivale | Snow mold, turf |
| Aphanomyces euteiches | Root rot, pea |

These pathogens include those that are most problematic to the agriculture, forest, and horticulture industries. Some of these pathogens do not currently have effective chemical controls (e.g. Sclerotium and Aphanomyces) or current chemical control measures directed against the pathogen will be terminated (e.g. bare-root nursery conifer pathogens such as Pythium, Fusarium, and Rhizoctonia).

The in vitro antagonism bioassay used to determine fungal pathogen inhibition considered of spot inoculating of the particular actinomycete spores, in triplicate, 10 mm from the center of a petri plate containing PDA. The spores were allowed to germinate and grow for seven days at 30° C. At this time, a 5 mm square fungal plug cut from an actively growing fungal culture was aseptically placed upside down in the center of the actinomycete-inoculated plate. The cultures were incubated at room temperature until the mycelia of the pathogen control plate (containing pathogen only) grew to the outer plate boundary. At this time, the fungal inhibition zone was measured. Bacterial pathogen bioassays consisted of inoculating a line of actinomycete spores down the center of a PDA plate extending to the plate's edge. Bacterial pathogens were inoculated perpendicular to the actinomycete line of spores adjacent to this line and extending to the plate's edge. The zone of inhibition was measured from the actinomycete growth line. Table 3 illustrates the range in antagonism of each member of ATCC 55984 elicited against nine of the tested pathogens.

TABLE 3

| Isolated strain # | F. oxysporum 9051C | P. ultimum | H. annosum | S. cepivorum | Rhizoctonia | [1]FORL B | P. terrestris | X. campestris | B. solanacearum |
| --- | --- | --- | --- | --- | --- | --- | --- | --- | --- |
| 125 | [2]6 | 1 | 1 | 5 | 4 | 2.5 | 2 | 0 | 0 |
| 226 | 6 | 2 | 1 | 0 | 5.3 | 4.4 | 6 | 0 | 1.7 |
| 230 | 7 | 2.5 | nd | 2.8 | 5 | 5 | 5.2 | 0 | 0 |
| 278 | 6 | 0 | 2.4 | 3 | 5.1 | 4.3 | 2.8 | 0 | 0.3 |
| 302 | 5 | 2 | 2.5 | 1.8 | 4.5 | 3.5 | 3.1 | 0 | 0 |
| 333 | 6 | 3.5 | 4.2 | 3 | 5.9 | 4.2 | 4.8 | 0 | 0 |
| 506 | 6.5 | 5 | 5.1 | 6 | 10 | 8 | 8 | 0 | 1 |
| 529 | 4.5 | 7.2 | 10 | 5.4 | 10 | 8.6 | 8 | 0 | 0 |
| 541 | 1 | 9 | 7.6 | 8.4 | 10 | 4.2 | 5.5 | 0.5 | 0.7 |
| 560 | 5 | 6.8 | 10 | 5.5 | 10 | 7.8 | 5.2 | 0 | 0 |
| 568 | 5.2 | 6.1 | 3.6 | 5.6 | 7.5 | 7 | 9 | 0 | 0 |
| 588 | 0.5 | 2.5 | 1 | 3.2 | 4.9 | 0 | 0.5 | 0 | 2.7 |
| 611 | 6 | 5 | 2.9 | 4 | 5.4 | 6 | 6 | 0 | 0 |
| 619 | 4 | 4 | 2.8 | 5.5 | 9 | 6.5 | 6.3 | 3.2 | 0 |
| 642 | 5 | 5.5 | 3 | 3.8 | 9.5 | 6 | 5.9 | 5.3 | 0 |
| 643 | 7 | 8 | 10 | 7.8 | 10 | 8 | 6.8 | 0 | 6 |
| 668 | 6 | 4 | 10 | 3.6 | 4.1 | 4 | 2.4 | 10 | 10 |
| 718 | 4 | 5 | 10 | 3.2 | 8 | 6 | 5.5 | 0 | 0 |
| 736 | nd | 5 | nd | 0 | 0 | 0 | 0 | 0 | 0 |
| 737 | 6 | 5 | 3.2 | 3.2 | 5 | 4.5 | 5 | 0 | 8 |
| 738 | nd | 0 | nd | 3 | 0 | 0 | 0 | 0 | 0 |
| 739 | nd | 8.5 | nd | 0 | nd | 0 | 0 | 0 | 0 |
| 741 | nd | 0 | 0 | 0 | 0 | 0 | 0 | 0 | 0 |
| 762 | nd | 4 | 1 | 5 | nd | 6 | 0 | 10 | 2.7 |

[1]FORL-B, *Fusarium oxysporum radicus lycopersici*, tomato crown and root rot.
[2]Values indicate relative inhibition of the pathogen due to antagonism by the actinomycete strain. A value of ten indicates total inhibition, no growth of the pathogen. A value of zero indicates the fungal colony grew directly adjacent or over the actinomycete colony indicating absence of pathogen inhibition. Intermediate values indicate intermediate antagonism levels. nd, not determined.

Table 3 is illustrative for three purposes. First, it indicates the high levels of antigonism elicited by these actinomycete strains against a wide variety of virulent pathogens. Second, the table taken in its entirety serves as a taxonomic tool in that each strain within the consortia is characterized by a unique set of measurements, characterizing that strain as a singular individual possessing different properties from all other strains. Third, it illustrates the value and novelty of incorporating mixtures of compatible strains into a single biological control product. One example is given for a mixture designated as AM-3 in the table containing strains 529, 541, and 560. Strain 541 elicits only minor antagonism against *F. oxysporum* 9051C but strains 529 and 560 elicit moderate to high levels against this pathogen. The situation is reversed in the case of antagonism against *S. cepivorum*, whereas 541 inhibits the growth of this pathogen almost completely, yet the other two strains show moderate antagonism. *P. terrestris* is almost completely antagonized by strain 529, but only moderately by 541 and 560. The differential antagonism of a mixture designated as AM-3a in the table comprised of strains 568, 611, and 642 illustrates another example. Strain 642 elicits strong antagonism against the bacterial pathogen *X. campestris*, whereas 568 and 611 do not affect the growth of this pathogen. Strains 568 and 611 elicit moderate to strong antagonism against the fungal pathogen *S. cepivorum*, whereas 642 moderately affects the growth of this organism. Due to these types of analyses and others to follow, our in vivo tests utilized mixtures of strains, thus providing a broader range of biological control effects.

In order for spore germination and vegetative growth of actinomycetes, water and carbon sources that can be assimilated by the organism must be available at the correct time and place. The heterotrophic ability of actinomycetes is well known. Yet individual strains differ in their ability to assimilate different carbon compounds. Table 4 below illustrates this fact.

isms for growth. Those microorganisms or strains that can efficiently capture these often-limited nutrient sources will competitively exclude those that cannot. There is advantage to using a single strain of actinomycete for biological control, but there is also advantage offered by a mixture of actinomycete strains provided as a single biological control formulation. A preferred carbon source of a particular microorganism in the mixture may become limited or may be absent altogether. The plant root's microenvironment will provide distinct carbon compounds that a different actinomycete strain in the mixture can readily assimilate. This extends the capacity of the biological control formulation to work effectively since a single mixture can protect a wider range of plants.

In table 5, antibiotic resistance profiles indicate that each actinomycete strain also possesses a distinct antibiogram. Thus each strain is unique. Furthermore, antibiotic resistance genes are closely clustered with antibiotic biosynthesis genes in actinomycetes. Therefore those strains eliciting resistance to a variety of antibiotics potentially may synthesize those antibiotics. It is apparent that a number of strains potentially produce a variety of antibiotics. The argument for utilizing mixtures of strains in a biological control formulation becomes apparent in that if one member of the consortium lacks the potential to produce a particular antibiotic that a pathogen may be susceptible to, another strain may synthesize the said antibiotic.

TABLE 4

[1]Carbon compounds most differentially utilized by the identified actinomycete strains

| Strain | D-melezitose | Arbutin | D-sorbitol | Xylitol | L-rhamnose | D-raffinose | Stachyose | α-methyl D-mannoside | L-pryoglutamic acid |
|---|---|---|---|---|---|---|---|---|---|
| 560 | 2 | 5 | 1 | 1 | 5 | 3 | 3 | 5 | 5 |
| 506 | 0 | 0 | 1 | 1 | 3 | 2 | 2 | 2 | 4 |
| 541 | 2 | 1 | 5 | 3 | 1 | 5 | 5 | 1 | 1 |
| 668 | 1 | 2 | 2 | 1 | 4 | 4 | 3 | 5 | 4 |
| 568 | 1 | 0 | 1 | 2 | 4 | 4 | 2 | 4 | 2 |
| 643 | 2 | 2 | 2 | 2 | 5 | 3 | 4 | 5 | 5 |
| 529 | 0 | 0 | 1 | 1 | 3 | 2 | 2 | 4 | 5 |
| 718 | 2 | 3 | 2 | 1 | 4 | 2 | 2 | 4 | 4 |
| 762 | 0 | 5 | 0 | 0 | 4 | 5 | 5 | 1 | 3 |
| 611 | 5 | 4 | 5 | 5 | 1 | 5 | 5 | 1 | 2 |
| 619 | 5 | 2 | 5 | 5 | 1 | 5 | 5 | 1 | 2 |

[1]100 μl of a spore suspension of each actinomycete stain was inoculated into each well of a single carbon source microtiter plate containing 95 wells with different carbon compounds (Biolog SF-P MicroPlate ™, Biolog, Inc.). This was done according to the manufacturer suggestion. Cultures were incubated at 30° C. for one week. Measurement values of growth were based on a 0–5 scale, 0 indicatingno growth and 5 indicated extensive mycelial ramification and subsequent sporulation. Intermediate values indicate intermediate growth based on relative growth characteristics.

The measurements indicate a specific carbon source utilization value for each strain, thus providing a "fingerprint" or identification profile unique for each of these organisms. Each strain is clearly unique in its ability to assimilate various carbon compounds.

Soils and the rhizospheres of different plants provide distinctly different carbon sources utilized by microorgan-

TABLE 5

| [1]Strain Antibiotic | 718 | 643 | 560 | 541 | 529 | 333 | 611 | 588 | 642 |
|---|---|---|---|---|---|---|---|---|---|
| Ap | 200 | 100 | 113 | 200 | 100 | 200 | 28.9 | 68.4 | 200 |
| Cb | 100 | 100 | 100 | 100 | 60.5 | 100 | 100 | 100 | 100 |
| Cp | 100 | 9.2 | 31.6 | 100 | 10.5 | 100 | 104 | 0 | 112 |
| Ca | 0 | 5.6 | 21.1 | 0 | 0 | 44.4 | 0 | 39.5 | 0 |
| Ct | 0 | 0 | 0 | 0 | 0 | 0 | 0 | 0 | 0 |
| Er | 34.2 | 0 | 0 | 76.3 | 0 | 27.6 | 22.4 | 52.6 | 32.9 |
| Gn | 0 | 0 | 0 | 0 | 0 | 0 | 0 | 0 | 6.6 |
| Kn | 0 | 0 | 0 | 0 | 0 | 0 | 0 | 0 | 0 |
| Ln | 200 | 200 | 200 | 200 | 138 | 200 | 200 | 200 | 200 |
| Nl | 0 | 0 | 0 | 0 | 0 | 0 | 0 | 42.1 | 0 |
| Nm | 42.1 | 0 | 0 | 0 | 0 | 30.3 | 35.5 | 0 | 0 |
| Nf | 100 | 44.7 | 0 | 100 | 0 | 100 | 100 | 100 | 78.9 |
| Nv | 0 | 27.6 | 32.9 | 0 | 7.9 | 0 | 0 | 0 | 0 |
| Ol | 100 | 17.1 | 46.1 | 125 | 19.7 | 21.1 | 0 | 100 | 100 |
| Ox | 0 | 0 | 0 | 0 | 0 | 21.1 | 0 | 22.4 | 0 |
| Pn | 0 | 56.7 | 44.4 | 100 | 12.2 | 66.7 | 100 | 0 | 39.5 |
| Pm | 0 | 15.6 | 10 | 143 | 0 | 200 | 100 | 100 | 100 |
| Rf | 0 | 0 | 0 | 0 | 7.9 | 0 | 0 | 100 | 0 |
| Sr | 0 | 0 | 0 | 61.8 | 0 | 0 | 0 | 0 | 0 |
| Tc | 0 | 0 | 0 | 0 | 0 | 32.9 | 0 | 100 | 0 |
| Tb | 0 | 0 | 0 | 22.4 | 0 | 0 | 0 | 0 | 0 |

[1]Antibiotic concentrations given in μg/ml. Values indicate the concentration at which the actinomycete strain is resistant to the particular antibiotic. Gradient plate technique used to determine resistance referred to by reference in Eisenstadt, E., et al. 1994. Gene Mutation. In: Methods for General and Molecular Biology. Gerhardt, P., R. G. E. Murray, W. A. Wood, and N. R. Kreig (eds.). American Society for Microbiology, Washington, D.C. p. 304.

Ap=ampicillin, Cb=carbenicillin, Cp=cephloradine, Ca=chloramphenicol, Ct=chlorotetracycline, Er=erythromycin, Gn=gentamycin, Kn=kanamycin, Ln=lincomycin, Nl=naladixic acid, Nm=neomycin, Nf=norfloxacine, Nv=novabiocin, Ol=oleandomycin, Ox=oxytetracycline, Pn=Penicillin, Pm=polymixin B, Rf=rifampicin, Sr=Streptomycin, Tc=tetracycline, Tb=tobramycin.

Spore stock cultures of these actinomycetes may be produced by inoculating, via spread plate, of PDA media is done from archived spore stock cultures. Plates are incubated at 30° C. until the cultures are well sporulated, usually in 2–3 weeks. Spores may then be mixed into a carrier or stored in 20% glycerol at −20° C. Spores will remain viable for months in zeolite at 4 to 25° C.

The 24 strains described herein can all be isolated from ATCC deposit 55984. Each of the 24 actinomycete isolates or strains possess unique properties, and taken as a whole this consortium is strongly antagonistic towards a broad range of phytopathogens, and it utilizes many different carbon sources, and it synthesizes a number of antibiotics. Each strain can be isolated and purified from this mixture by utilizing knowledge of each strain's unique growth habits and antibiotic resistance profiles. FIG. 1 illustrates the manner in which the purification may be accomplished. The labeled arrows indicate the specific media, antibiotic, or culture conditions, which are specific for each individual strain. Antibiotic concentrations are given in parenthesis. Single carbon compounds are supplied as 5% solutions (final concentration), filter sterilized, and amended into an autoclaved base medium comprised of $K_2HPO_4$ (0.5 g/L), $MgSO_4 7H_2O$ (0.2 g/L), NaCl (0.1 g/L), $(NH_4)_2SO_4$ (0.5 g/L), and yeast extract (trace) pH 7.0. Carbon sources not described in FIG. 1 are specified here as 5% putrescine-HCl or one-half strength PDA.

Fatty acid profiles were generated from a number of the strains within the consortia ATCC 55984 by Microbial ID, Inc., Newark, Del. 19711. Library matches to their bacteria database indicated that matches occurred mostly within the *Streptomyces genera*. (table 6).

TABLE 6

SUMMARY OF MICROBIAL IDENTIFICATION SYSTEM

| Strain # | Identification | [1]Similarity Index |
|---|---|---|
| 205 | Streptoverticillium cinnamonem | 0.022 |
| 261 | Streptomyces[2] v. violaceusniger | 0.353 |
| 333 | Streptomyces v.[3]h. ossamyceticus | 0.324 |
| 503 | Streptomyces halstedii | 0.050 |
| 506 | Streptomyces v. violaceusniger | 0.198 |
| 515 | Streptomyces v. violaceusniger | 0.485 |
| 520 | Streptomyces halstedii | 0.032 |
| 529 | Streptomyces v. violaceusniger | 0.248 |
| 541 | Streptomyces halstedii | 0.041 |
| 560 | Streptomyces cyaneus | 0.019 |
| 575 | Streptomyces v.h. ossamyceticus | 0.286 |
| 588 | Streptomyces lavendulae | 0.473 |
| 611 | Streptomyces v.h. ossamyceticus | 0.394 |
| 619 | Streptomyces lavendulae | 0.443 |
| 642 | Streptomyces v.h. ossamyceticus | 0.343 |
| 643 | Streptomyces v. violaceusniger | 0.309 |
| 662 | Streptomyces v.h. ossamyceticus | 0.431 |
| 664 | Streptomyces v. violaceusniger | 0.154 |
| 718 | Streptomyces v.h. ossamyceticus | 0.445 |
| 762 | Streptomyces v. violaceusniger | 0.411 |
| 675 | Streptomyces halstedii | 0.074 |
| 676 | Streptomyces v. violaceusniger | 0.450 |
| Environmental Isolate | Streptomyces v. violaceusniger | 0.680 |
| Environmental Isolate | Streptomyces v. violaceusniger | 0.352 |
| Environmental Isolate | Streptomyces anulatus | 0.273 |

[1]Microbial identification is based on a similarity index. The similarity index is a numerical value which expresses how closely the fatty acid composition of an unknown strain compares with the mean fatty acid composition of the strains compiled by Microbial ID, Inc. in their databases. Strains with a similarity of 0.500 or higher indicate good matches. Strains with a similarity index between 0.300 and 0.500 may be a good match but is an atypical strain (common with environmental isolates), and values lower than 0.300 suggest the species is not in the database but those listed provide the most closely related species.

2 v=*violaceusniger*

3 h=*halstedii*

Figure 2:
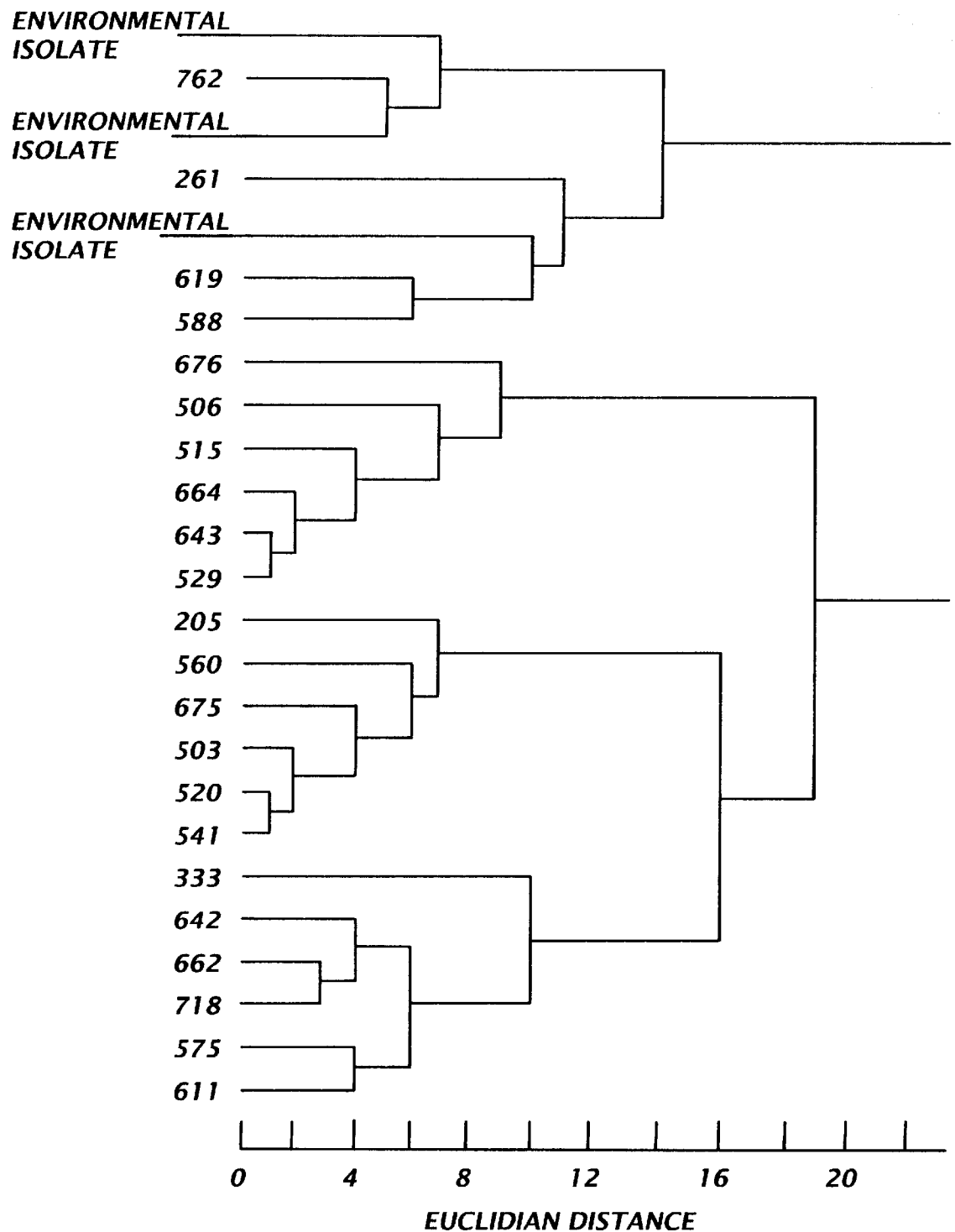
FIG. 2 is a dendogram generated from fatty acid profiles demonstrating that the strains of Actinomycete in the present invention are unique from each other, based on the dendogram and additional factors.

A dendogram was developed describing the relationships between some strains of the consortium ATCC 55984 (FIG. 2). Table 6 and FIG. 2 serve to illustrate that even though strains of the consortia may be members of the same species, they are clearly not the same strains based on calculated euclidian distances, antibiograms, carbon utilization patterns, and antagonism profiles. It is clear that these are unique strains with novel biological control properties.

Examples of isolating the described strains from the consortium ATCC 55984 and specific in vitro experiments illustrating the biological control capabilities of this invention are shown by the following examples.

EXAMPLE 1

Isolation of a Strain of Actinomycete From ATCC 55984 and Isolation of a Substance From a Strain An example of the method used for isolation of a single strain from the consortium ATCC 55984 (IBS-24) is provided for isolation of strain 643. IBS-24 is plated on agar base medium amended with the single carbon source 3-methyl glucose, 5.0% (final concentration). The plating may be done either as streak inoculation of the entire mixture, or as dilution plating. 3-methyl glucose provides a carbon source specific for strains 643, 529, 718, and 611 (FIG. 1). Plates are incubated at 30° C. for two weeks or until all colonies are well-sporulated. Isolated colonies from either the streak-inoculated plates or the dilution plates are picked and streak-inoculated onto agar media containing novabiocin (25 µg/ml, final concentration) and norfloxacine (40 µg/ml, final concentration). The carbon source for the agar media may be ½ strength PDA, or base media consisting of 5% 3-methyl glucose or 5% putrescine-HCl (media amenable to growth of any or all strains within IBS-24 or of strains 643, 529, 718, or 611 as is the case with 3-methyl glucose). The novabiocin and norfloxacine at the specified concentration are specific for isolation of strain 643 due to its tolerance of these antibiotics at the listed concentrations. Plates are incubated for two weeks or until colonies are well-sporulated. At this point, all colonies which become evident are of strain 643 due to its unique physiological growth nature.

Additionally, substances characteristic of a strain can be isolated by lysis of a spore or mycelia cell wall and membrane of the strain, and organic acid extraction of the resulting cell constituents, and ethanol precipitation of the aqueous phase of the cell constituents.

EXAMPLE 2

In Vitro Antagonism of Fungal Phytopathogens by Individual Actinomycetes Strains In order to further screen for the biological control potential of the actinomycetes which elicited greatest antagonism against pathogens on the plate antagonism bioassays, thirty-eight actinomycete isolates were mixed as a spore inoculum, into sterilized peat-vermiculite mixture, Black Gold™ (Black Gold, Inc., Hubbard, Oreg.). *Fusarium oxysporum* Schlechtend.:Fr. f.sp. radicus-lycopersici W. R. Jarvis & Shoemaker (FORLB) chlamydospores to be used for pathogenicity and in vivo antagonism tests were prepared using a modification of the method of James et al. (James et al., 1989). An aluminum metal pan was filled with 75 g of Black Gold potting mix and amended with 75 g yellow corn meal. This material was mixed and autoclaved twice for 45 minutes. Warm, 1% PDA agar was added to the mixture and mixed with 1 cm² actively growing agar plugs of Fusarium (two standard PDA plates). The pathogen was grown, covered, for a month at room temperature, air-dried, blended, and its spore population determined by dilution plating onto PDA agar. This method produced viable spores that were stored at room temperature.

A single actinomycete ($1 \times 10^5$ CFU/g final concentration) and fungal spore ($1.25 \times 10^3$ CFU/g) preparation were combined into the peat-vermiculite mixture. This material was wetted with sterile water under negative pressure in order to hydrate the peat. The mixture was then placed into a wedge within 8L polycarbonate (Nalgene) chambers, with 10 separate treatments/chamber. Air circulation was provided by polyurethane-plugged vents cut into the side and into the removable top plate of the chamber. Surface sterilized tomato (*Lycopersicon esculentum* Mill.) 'Better Boy' seeds were sown into the FORLB treatments (9 seeds/treatment). Controls consisted of unamended peat-vermiculite or pathogen only treatments. Gypsum soil moisture blocks (Davis Instruments, Baltimore, Md., model KS-D1) were placed in each chamber to monitor water potential.

Seedlings were grown at room temperature under natural light. Degree of fungal growth and general plant health were visually monitored at periodic intervals, as was seedling emergence. At one month, plants were harvested, the root tips cut (0.5 cm lengths), washed in sterile water, and plated on PDA amended with cyclohexamide and nystatin (50 mg/L) and polymyxin B (5 mg/L). Previous results indicated all actinomycete strains tested were resistant to these antibiotics. Plates were incubated at 30° C. for two weeks and monitored for actinomycete outgrowth from the root tip sections onto the agar surface. Each treatment was analyzed for actinomycete and fungal counts in the bulk soil by dilution plating. 1.5 g of homogeneously mixed treatment soil was placed in 30 ml sterile phosphate buffer ($10^{-1}$ dilution) and shaken for 30 minutes on a wrist action shaker. Serial dilutions were performed and suspensions plated on Peptone-PCNB agar (Nash and Snyder, 1962) for fungal counts and PDA amended with cyclohexamide, nystatin, and polymyxin B for actinomycete quantitation.

TABLE 7

| Strain | [1]Actinomycete CFU/g $1 \times 10^5$ | [2]Fungal counts CFU/g $1 \times 10^5$ | % Seed germination | % Seedlings Post-damped | Actinomycete root colonization |
|---|---|---|---|---|---|
| 588 | 27 | 5 | 56 | 100 | [3]nd |
| 642 | 37 | 31 | 78 | 100 | nd |
| 643 | 0 | 25 | 44 | 100 | nd |
| 737 | 40 | 10 | 33 | 100 | nd |
| [4]FORL B | 0 | 38 | 44 | 89 | no |
| [5]226 | 0 | 10.5 | 89 | 33 | no |
| 278 | >300 | 11.7 | 67 | 33 | no |
| 302 | 128 | 7.6 | 78 | 33 | no |
| 333 | 20 | 7.7 | 67 | 33 | yes |
| 529 | 0 | 4.9 | 89 | 44 | yes |
| 541 | 186 | 6.3 | 100 | 22 | yes |
| 560 | 21 | 7.0 | 100 | 66 | yes |
| 568 | 0 | 8.3 | 100 | 89 | yes |
| 611 | 0 | 6.7 | 89 | 66 | yes |
| 619 | 8 | 6.0 | 100 | 56 | no |
| 643 | 0 | 7.4 | 89 | 44 | yes |
| 668 | 0 | 5.6 | 100 | 56 | yes |
| 718 | 4 | 6.2 | 67 | 78 | yes |
| 762 | 1 | 4.3 | 78 | 56 | Yes |
| FORL B | 0 | 5.6 | 67 | 89 | no |

[1]Soil dilution plate counts on soil-less potting mix, average number of actinomycete colonies recorded at $1 \times 10^5$ CFU/g.
[2]Soil dilution plate counts on soil-less potting mix, average number of Fusarium colonies recorded at $1 \times 10^5$ CFU/g.
[3]nd = not determined.
[4]Pathogen only control.
[5]Second series of experiments performed independently of the other experiments with those strains listed above strain 226 in the table.

A number of individual actinomycete strains elicited strong in vivo inhibition of Fusarium root rot disease determined by significant increases in percent seed germination and a corresponding decrease in post-damping effects as compared to the Fusarium control plants. A number of these same strains colonize the roots of the tomato seedlings, thus would be prevalent upon seedling transplants.

EXAMPLE 3

Summary of Select Field and Greenhouse Trials with Biological Control Actinomycetes Actinomycete isolates were extensively tested in greenhouse and field trials to determine the extent of biological control derived under large-scale practical field conditions. A summary of the benefits in yield, decrease in disease symptoms, or morphological plant gains is illustrated in table 8.

TABLE 8

| Crop | Trial Size | Where | Type of Trt. and strains used | Trend or Significance | $ or % of Effect |
|---|---|---|---|---|---|
| Potato, Russet Burbank | Small Plot (35 pieces/ trt) | Idaho Falls, ID | Seed piece coat AM-3 | Highest stand counts. Highest vigor rating. Bottom ⅓ in % Rhizoctonia lesions, decay, and rot. Increased yield | Total yield represents 9.2% increase over control or approx. $160/acre. |
| Onion, Walla Walla Sweet | 42,217 sets planted | Walla Walla, WA | Drench application AM-6 | 67,400 emergence counts (treated) vs. 60,000 for control (statistically significant) | Emergence corresponds to $500/acre increase |
| Rex Yellow dry | 3 acres | Palouse | Seed coat AM-6 | 39% increase in emergence over control (statisti-cally significant) | Emergence corresponds to $3/acre increase |
| Lentils, Brewer | 6.6 acres | Palouse | Seed coat AM-6 | 8.3% increased yield over control (statistically significant) | $4.4/acre increase in yield |
| Grapes, Johannesburg Reisling | Small field | CA | Phylloplane spray AM-6 | 30% decrease in Botrytis bunch rot (statistically significant) | Represents $640/acre in value increase over controls |
| Tomato, 'Sunny' | Small Scale Chamber | FL | Peat moss application AM-3a | 8.8% increase in plant height, 26% increase in shoot wt., 1.7 orders of magnitude decrease in FORL B incidence | |
| Western Larch | Greenhouse 6,400 seedlings | Univ. of Idaho | Peat moss application AM-4 | 52% decrease in Fusarium disease incidence (Statistically significant) | $6,500 savings per 100,000 seedlings |

Additional Actinomycete mixtures used in the trials include a mixture of strains 333, 529, 541, 560, 643, and 718, and identified in the table as AM-6. A mixture identified in the table as AM-4 which contained strains 588, 611, 718, and 739 was also tested in this example.

Enhancements in plant vigor or yield as a consequence of actinomycete amendment were achieved under pathogen stress. Either field soils were chosen which had been problematic to the host plant in the past due to high pathogen concentrations, or the planting medium and seeds were challenged directly with pathogens. Details of some of these trials follow.

EXAMPLE 4

Potato Small Plot Trials

Two actinomycete applications were compared to fungicide and pathogen inoculated potatoes in the 1996 potato seedpiece treatment summer field trials at the University of Idaho Cooperative Extension Station, Idaho Falls, Id. under the direction of Dr. P. Nolte and W. Jones. Potato seedpieces were inoculated with talc-actinomycete mixtures AM-6 and AM-3. In this trial, 175 seedpieces were coated with 3 kg talc-actinomycete mixture at $4.4 \times 10^6$ spores/g carrier.

Thirty-five seedpieces/plot of G2 Russet Burbank from the University of Idaho Tetonia R & E Center were planted on May 9, 1996. The plot consisted of 35 foot rows with five replications in a randomized complete block design. *Fusarium sambucinum* Isolate FID-212 (North Dakota State Univ.) was inoculated (8 ml water suspension at $1 \times 10^6$ CFU/ml per 180 seedpieces) in all treatments except the untreated uninoculated control, to evaluate Fusarium seed piece decay. Nitrogen fertilizer (N=150 lbs.) was applied to the test plot. Also, 4 pt. Eptam+0.25 lb. Sencor as a tank mix was applied post-emergence as a herbicidal treatment. Potatoes were irrigated throughout the growing season.

Stand evaluations (number of plants emerged) were performed on Jun. 25, 1996. Early-season performance evaluations were taken on Jul. 28, 1996. These evaluations consisted of vigor determinations (based on a 0–4 scale), number stems/tuber, rhizoctonia incidence (percent stems with Rhizoctonia lesions), and seed piece decay (estimated percent decay/seedpiece). The early season performance ratings were based on destructive sampling of 10 seedpieces from each plot (for a total of 10 seedpieces/plot, 50 seedpieces/treatment). Yield and grade data were collected on the remaining 25 seedpieces/plot at the time of harvest. At this time, decay (estimated percent decay/seedpiece) and rot (log 10 (decay+1)) were measured. Treatment means were separated by LSD (p=0.05) following statistical analysis by ANOVA.

Potatoes treated with mixture AM-3 consistently rated high in the response measurements including stand, vigor (table 9), and yield. Stand and yield measurements were not statistically different from other response variables at the p=0.05 level. Potatoes inoculated with AM-6 and AM-3 mixtures rated second and fourth lowest on per cent of stem Rhizoctonia disease (data not shown) but they were not statistically significant (p=0.05 level) from the other treatments. Potatoes inoculated with AM-3 also had one of the lowest ratings on the rot index (table 9) and elicited the lowest measurement on number of culls, but again the data was not statistically significant at the p=0.05 level. The stem index rating should fall within 3–4 (P. Nolte, personal communication) which corresponds to an optimal grade of tuber at harvest. Potatoes with AM-3 treatment fall well within this range (data not shown).

TABLE 9

| | Statistical values | Mean | Treatment |
|---|---|---|---|
| [1]Vigor Description statistics | | | |
| Alpha | 0.05 | [2]3.66 a | AM-3 |
| df | 578 | 3.56 ab | [3]Mancozeb |
| MSE | 0.426 | 3.50 abc | [4]Maxim |
| Critical Value of T | 1.96 | 3.34 | Untreat. uninoculated |
| LSD | 0.260 | 3.32 bcd | AM-6 |
| Harmonic Mean | 49.0 | 3.32 bcd | [5]Captan |
| | | 3.32 bcd | Carrier control |
| | | 3.32 bcd | [6]Single drop |
| | | 3.26 dc | [7]Untreat. Inoc. |
| | | 3.22 d | [8]TBZ |
| [9]Rot Descriptive statistics | | | |
| Alpha | 0.05 | 0.709 a | TBZ |
| df | 576 | 0.703 a | Carrier control |
| MSE | 0.319 | 0.675 a | Untreat. Inoc. |
| Critical value of T | 1.96 | 0.513 ab | Untreat. Uninoc. |
| LSD | 0.225 | 0.488 ab | AM-6 |

TABLE 9-continued

| | Statistical values | Mean | Treatment |
|---|---|---|---|
| Harmonic mean | 48.82 | 0.449 b | Captan |
| | | 0.436 b | AM-3 |
| | | 0.352 b | Single drop |
| | | 0.082 c | Mancozeb |
| | | 0.055 c | Maxim |

[1]Potato vigor based on a 0–4 scale; 0 = not emerged, 4 = excellent.
[2]Means with the same letter are not statistically significant.
[3,4,5,8]Standard potato chemical fungicide treatments.
[5]Single drop potatoes are uncut seed potatoes.
[7]Untreated, inoculated is the control inoculated with pathogen, but not treated with carrier or any other chemical or biological amendments. All other treatments were inoculated with the pathogen except for the untreated, uninoculated control.
[9]Rot calculated as log10(decay + 1) whereas decay = estimated percent decay/seedpiece.

EXAMPLE 5

Onion Field Trials 0.268 acres of Walla Walla sweet seed onions were treated with mixture AM-6 as a furrow spray application at the time of planting, Sep. 16, 1996, near Walla Walla, Wash. The spore-zeolite stock inoculum was passed through 170 mesh screen prior to application to ensure the spray nozzles would not clog during application. The inoculum was added to powdered milk as a solubilizable carrier (114 g inoculum+ 250 g powdered dry milk). The formulation was suspended in 15 gallons of water and applied to the onions as they were sown. The spray was applied to three blocks, each block consisting of 180 linear feet (eight double-seeded rows) for a total of 34,560 onions. Approximately $6 \times 10^5$ CFU were placed in the furrow/seed. The experimental design consisted of three blocks of three (8 double row by 60 foot) onion replications. Powdered milk-sieved zeolite carrier constituted the control rows.

Emergence counts were taken on 2 months post-planting. All seedlings were counted in two of the eight double seeded rows within each 60 foot row. Treatment means were separated and analyzed statistically.

Emergence was enhanced significantly in response to actinomycete drench inoculum. The mean emergence of the actinomycete-inoculated onion sets/row was 125 as compared to 112 for the blank control rows. This relates to 67,400 onions/acre vs. 60,000/acre in the control. The field plot has had significant pink root, white rot, and smut problems in the past. A combination of these factors could account for the lower emergence incidence in the control plots.

EXAMPLE 6

Decrease in Fusarium Disease on Western Larch Large-Scale Greenhouse Trial

Four actinomycete mixtures and a carrier only control were inoculated into a soil-less peat/vermiculite potting mix used for container-grown Western Larch seedlings. The actinomycete mixtures consisted of AM-3, AM-4, a mixture identified as Con-5 in the tables, (Con-5 contains strains 333, 588, 611, 642, and 737), and a mixture identified in the tables as Con-3 (Con-3 contains strains 333, 619, and 643). The actinomycete spores were inoculated to a final concentration of $1 \times 10^6$ CFU/g potting mix. The Western larch seeds were challenged with two species of pathogen spores at three concentrations. Fusarium oxysporum 9051C spores were produced as referred to previously at $1 \times 10^6$, $1 \times 10^5$, and $1 \times 10^4$ CFU/g potting mix. Fusarium proliferatum 9202F spores were inoculated into the potting mix in an identical manner. 6,400 seedlings were monitored for emergence, damping-off, actinomycete and Fusarium root colonization, and disease symptoms throughout the growing season.

Table 10 summarizes the results of this large scale greenhouse trial.

TABLE 10

| [1]Means of Western Larch disease rating | [2]Means of Western Larch root/shoot ratios | [3]Actinomycete numbers in peat/vermiculite |
|---|---|---|
| [4]Carrier control 1.57 a | AM-3 3.05 a | AM-3 a |
| Con-5 1.16 b | Con-5 2.97 ab | Con-5 a |
| AM-3 1.06 bc | Con-3 2.75 bc | AM-4 b |
| Con-3 0.99 bc | AM-4 2.74 bc | Con-3 c |
| AM-4 0.75 c | Carrier control 2.54 cd | Carrier control d |

[1]Disease rating based on a 1–5 scale, 1 = no disease symptoms, 5 = dead seedling.
[2]Mass of dry root/mass of dry stem.
[3]Means separation based on ranked data.
[4]Means with the same lower case letter are not statistically significant Disease symptoms elicited by the conifer pathogen Fusarium oxysporum 9051C decreased by up to 52% on the actinomycete inoculated seedlings. The higher root/shoot ratios also indicate that the actinomycete inoculated seedlings were more vigorous as a result of healthier root systems. Actinomycete numbers remained high on roots (data not shown) and in the soil-less potting mix after 6–7 months post-inoculation.

Whereas particular embodiments of the invention have been described hereinabove, for purposes of illustration, it will be evident to those skilled in the art that numerous variations of the details may be made without departing from the invention as defined in the appended claims.

The present invention is not limited to the descriptions of specific embodiments presented hereinabove, but rather the present invention should be viewed in terms of the claims that follow and equivalents thereof. Further, while the invention has been described in conjunction with several such specific embodiments, it is to be understood that many alternatives, modifications, and variations will be apparent to those skilled in the art in light of the foregoing detailed descriptions. Accordingly, this invention is intended to embrace all such alternatives, modifications, and variations which fall within the spirit and scope of the appended claims.

REFERENCES

James, R. L., R. K. Dumroese, C. J. Gilligan, and D. L. Wenny. 1989. Pathogenicity of Fusarium isolates from Douglas-fir seed and container-grown seedlings. Bulletin No. 52. Idaho Forest, Wildlife and Range Experiment Station, Moscow, Id.

Nash, S. M. and W. C. Synder. 1962. Quantitative estimations by plate counts of propagules of the bean root rot Fusarium in field soils. Phytopathology. 52:567–572.

I claim:

1. A mixed culture of Actinomycetes having all of the identifying characteristics of the biologically pure mixed culture deposited as ATCC 55984.

2. A biologically pure culture of an Actinomycete having all of the identifying characteristics of an Actinomycete strain isolated from the mixed culture deposited as ATCC 55984.

3. A biologically pure culture of an Actinomycete having all of the identifying characteristics of an Actinomycete strain isolated from the mixed culture deposited as ATCC 55984, wherein the strain is 125, 226, 230, 278, 302, 333, 506, 529, 541, 560, 568, 588, 611, 619, 642, 643, 668, 718, 736, 737, 739, 741 or 762.

4. The biologically pure culture of claim 3, wherein the strain confers protection against a fungal or bacterial pathogen in a susceptible plant.

5. The biologically pure culture of claim 3, wherein the strain enhances plant growth in a responsive plant.

6. A composition consisting essentially of a biologically pure culture having all of the identifying characteristics of at least one Actinomycete strain isolated from the mixed culture deposited as ATCC 55984, wherein the strain is selected from the group consisting of 125, 226, 230, 278, 302, 333, 506, 529, 541, 560, 568, 588, 611, 619, 642, 643, 668, 718, 736, 737, 739, 741 and 762, and a suitable delivery medium.

7. The composition of claim 6, wherein the composition confers protection against a fungal or bacterial pathogen in a susceptible plant.

8. The composition of claim 6, wherein the composition enhances plant growth in a responsive plant.

9. A composition consisting essentially of a biologically pure culture having all of the identifying characteristics of at least two Actinomycete strains isolated from the mixed culture deposited as ATCC 55984, wherein the strains are selected from the group consisting of 125, 226, 230, 278, 302, 333, 506, 529, 541, 560, 568, 588, 611, 619, 642, 643, 668, 718, 736, 737, 739, 741 and 762, and a suitable delivery medium.

10. The composition of claim 9, wherein the composition confers protection against a fungal or bacterial pathogen in a susceptible plant.

11. The composition of claim 9 wherein the composition enhances plant growth in a responsive plant.

12. A composition consisting essentially of a biologically pure culture having all of the identifying characteristics of at least three Actinomycete strains isolated from the mixed culture deposited as ATCC 55984, wherein the strains are selected from the group consisting of 125, 226, 230, 278, 302, 333, 506, 529, 541, 560, 568, 588, 611, 619, 642, 643, 668, 718, 736, 737, 739, 741 and 762, and a suitable delivery medium.

13. The composition of claim 12, wherein the composition confers protection against a fungal or bacterial pathogen in a susceptible plant.

14. The composition of claim 12 wherein the composition enhances plant growth in a responsive plant.

15. A composition consisting essentially of a biologically pure culture having all of the identifying characteristics of at least six Actinomycete strains isolated from the mixed culture deposited as ATCC 55984, wherein the strains are selected from the group consisting of 125, 226, 230, 278, 302, 333, 506, 529, 541, 560, 568, 588, 611, 619, 642, 643, 668, 718, 736, 737, 739, 741 and 762, and a suitable delivery medium.

16. The composition of claim 15, wherein the composition confers protection against a fungal or bacterial pathogen in a susceptible plant.

17. The composition of claim 15 wherein the composition enhances plant growth in a responsive plant.

18. A method of inhibiting infection by a fungal or a bacterial pathogen in a plant comprising:

contacting soil for growing the plant, a soil-less potting mixture for growing the plant or at least one plant part with a composition consisting essentially of a biologically pure culture having all of the identifying characteristics of one or more Actinomycete strains isolated from the mixed culture deposited as ATCC 55984, and a suitable delivery medium, wherein the strain is selected from the group consisting of 125, 226, 230, 278, 302, 333, 506, 529, 541, 560, 568, 588, 611, 619, 642, 643, 668, 718, 736, 737, 739, 741 and 762.

19. A method of enhancing plant growth, the method comprising:

contacting a substrate for growing a plant or at least one plant part with a composition consisting essentially of a biologically pure culture having all of the identifying characteristics of one or more Actinomycete strains isolated from the mixed culture deposited as ATCC 55984, and a suitable delivery medium, wherein the strain is selected from the group consisting of 125, 226, 230, 278, 302, 333, 506, 529, 541, 560, 568, 588, 611, 619, 642, 643, 668, 718, 736, 737, 739, 741 and 762; and wherein the substrate is selected from the group consisting of soil for growing the plant and a soil-less potting mixture.

* * * * *